US011154230B2

(12) United States Patent
Sullivan et al.

(10) Patent No.: US 11,154,230 B2
(45) Date of Patent: Oct. 26, 2021

(54) WEARABLE CARDIOVERTER DEFIBRILLATOR HAVING REDUCED NOISE PROMPTS

(71) Applicant: West Affum Holdings Corp., Grand Cayman (KY)

(72) Inventors: Joseph L. Sullivan, Kirkland, WA (US); Jaeho Kim, Redmond, WA (US)

(73) Assignee: WEST AFFUM HOLDINGS CORP., Grand Cayman (KY)

( * ) Notice: Subject to any disclaimer, the term of this patent is extended or adjusted under 35 U.S.C. 154(b) by 493 days.

(21) Appl. No.: 15/861,463

(22) Filed: Jan. 3, 2018

(65) Prior Publication Data

US 2018/0184933 A1 Jul. 5, 2018

Related U.S. Application Data

(60) Provisional application No. 62/442,919, filed on Jan. 5, 2017.

(51) Int. Cl.
*A61B 5/31* (2021.01)
*A61B 5/316* (2021.01)
(Continued)

(52) U.S. Cl.
CPC ............ *A61B 5/316* (2021.01); *A61B 5/6805* (2013.01); *A61N 1/3904* (2017.08);
(Continued)

(58) Field of Classification Search
CPC . A61B 5/04018; A61B 5/0432; A61B 5/6805; A61N 1/0484; A61N 1/3904; A61N 1/3925; A61N 1/3968
See application file for complete search history.

(56) References Cited

U.S. PATENT DOCUMENTS 3,724,355 A 4/1973 Busch et al.
3,724,455 A 4/1973 Linger
(Continued)

FOREIGN PATENT DOCUMENTS

DE 102005060985 A1 6/2007
EP 2305110 B1 4/2018
(Continued)

OTHER PUBLICATIONS

Klein, Helmut U. et al., Risk Stratification for Implantable Cardioverter Defibrillator Therapy: The Role of the Wearable Cardioverter-Defibrillator, Clinical Update, European Heart Journal, May 31, 2013, 14 pages, European Society of Cardiology, France.
(Continued)

*Primary Examiner* — Amanda K Hulbert
(74) *Attorney, Agent, or Firm* — Christensen O'Connor Johnson Kindness PLLC

(57) ABSTRACT

A wearable cardioverter defibrillator (WCD) including a support structure configured to be worn by an ambulatory patient, an energy storage module configured to store an electrical charge, a discharge circuit coupled to the energy storage module, electrodes configured to render an electrocardiogram (ECG) signal of the patient while the patient is wearing the support structure, a user interface configured to output an alarm in response to a noise alarm signal, and a processor. The processor is configured to receive the ECG signal, determine whether noise is present on the ECG signal, determine from the ECG signal whether a shock criterion is met, and cause the user interface to generate the noise alarm signal when the noise is present on the ECG signal and the shock criterion is met and not generate the noise alarm signal when noise is present on the ECG signal and the shock criterion is not met.

12 Claims, 7 Drawing Sheets

(51) Int. Cl.
*A61N 1/39* (2006.01)
*A61B 5/00* (2006.01)
A61N 1/04 (2006.01)
A61B 5/333 (2021.01)

(52) U.S. Cl.
CPC ............ *A61N 1/3925* (2013.01); *A61B 5/333* (2021.01); *A61N 1/0484* (2013.01); *A61N 1/3968* (2013.01)

(56) References Cited

U.S. PATENT DOCUMENTS

| | | |
|---|---|---|
| 4,583,524 A | 4/1986 | Hutchins |
| 4,619,265 A | 10/1986 | Morgan et al. |
| 4,666,432 A | 5/1987 | McNeish et al. |
| 4,698,848 A | 10/1987 | Buckley |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bomn et al. |
| 5,353,793 A | 10/1994 | Bornn |
| RE34,800 E | 11/1994 | Hutchins |
| 5,394,892 A | 3/1995 | Kenny et al. |
| 5,405,362 A | 4/1995 | Kramer et al. |
| 5,429,593 A | 7/1995 | Matory |
| 5,474,574 A | 12/1995 | Payne et al. |
| 5,618,208 A | 4/1997 | Crouse et al. |
| 5,662,690 A | 9/1997 | Cole et al. |
| 5,708,978 A | 1/1998 | Johnsrud |
| 5,741,306 A | 4/1998 | Glegyak et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,280,461 B1 | 8/2001 | Glegyak et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder et al. |
| 6,427,083 B1 | 7/2002 | Owen et al. |
| 6,450,942 B1 | 9/2002 | Lapanashvili et al. |
| 6,526,303 B1 | 2/2003 | Scampini |
| 6,529,875 B1 | 3/2003 | Nakajima et al. |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,753,759 B2 | 7/2010 | Pintor et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,527,028 B2 | 9/2013 | Kurzweil et al. |
| 8,548,557 B2 | 10/2013 | Garstka et al. |
| 8,560,044 B2 | 10/2013 | Kurzweil et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,706,215 B2 | 4/2014 | Kaib et al. |
| 8,706,255 B2 | 4/2014 | Phillips et al. |
| 8,738,130 B2 | 5/2014 | Freeman et al. |
| 8,742,349 B2 | 6/2014 | Urbon et al. |
| 8,897,860 B2 | 11/2014 | Volpe et al. |
| 8,904,214 B2 | 12/2014 | Volpe et al. |
| 8,949,077 B2 | 2/2015 | Fu et al. |
| 8,965,500 B2 | 2/2015 | Macho et al. |
| 9,008,801 B2 | 4/2015 | Kaib et al. |
| 9,084,583 B2 | 7/2015 | Mazar et al. |
| 9,089,685 B2 | 7/2015 | Sullivan et al. |
| 9,119,547 B2 | 9/2015 | Cazares et al. |
| 9,131,901 B2 | 9/2015 | Volpe et al. |
| 9,132,267 B2 | 9/2015 | Kaib |
| 9,265,432 B2 | 2/2016 | Warren et al. |
| 9,345,898 B2 | 5/2016 | Piha et al. |
| 9,408,548 B2 | 8/2016 | Volpe et al. |
| 9,445,719 B2 | 9/2016 | Libbus et al. |
| 9,454,219 B2 | 9/2016 | Volpe et al. |
| 9,579,020 B2 | 2/2017 | Libbus et al. |
| 9,591,983 B2 | 3/2017 | Amir et al. |
| 9,592,403 B2 | 3/2017 | Sullivan |
| 9,598,799 B2 | 3/2017 | Shoshani et al. |
| 9,675,804 B2 | 6/2017 | Whiting et al. |
| 9,724,008 B2 * | 8/2017 | Sullivan ............... A61N 1/3987 |
| 9,878,171 B2 | 1/2018 | Kaib |
| 9,888,858 B2 * | 2/2018 | Farrugia ............... A61B 5/0408 |
| 9,895,105 B2 | 2/2018 | Romem |
| 9,901,741 B2 | 2/2018 | Chapman et al. |
| RE46,926 E | 7/2018 | Bly et al. |
| 10,016,613 B2 | 7/2018 | Kavounas |
| 10,076,656 B2 | 9/2018 | Dar et al. |
| 10,192,387 B2 | 1/2019 | Brinig et al. |
| 10,307,133 B2 | 6/2019 | Kaib |
| 10,463,867 B2 | 11/2019 | Kaib et al. |
| 10,589,110 B2 | 3/2020 | Oskin et al. |
| 10,599,814 B2 | 3/2020 | Landrum et al. |
| 2002/0181680 A1 | 12/2002 | Linder et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0144355 A1 | 6/2013 | Macho et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0046391 A1 | 2/2014 | Cowan et al. |
| 2014/0070957 A1 | 3/2014 | Longinotti-Buitoni et al. |
| 2014/0163663 A1 | 6/2014 | Poddar et al. |
| 2014/0207201 A1 | 7/2014 | Piha et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0161554 A1 | 6/2015 | Sweeney et al. |
| 2015/0297135 A1 | 10/2015 | Shoshani et al. |
| 2015/0328472 A1 | 11/2015 | Sullivan et al. |
| 2016/0004831 A1 | 1/2016 | Carlson et al. |
| 2016/0045003 A1 | 2/2016 | Chen |
| 2016/0067514 A1 | 3/2016 | Sullivan |
| 2016/0076175 A1 | 3/2016 | Rock et al. |
| 2016/0076176 A1 | 3/2016 | Rock et al. |

(56) References Cited

U.S. PATENT DOCUMENTS

| | | |
|---|---|---|
| 2016/0082277 A1 | 3/2016 | Foshee, Jr. et al. |
| 2016/0113581 A1 | 4/2016 | Amir et al. |
| 2016/0256104 A1 | 9/2016 | Romem et al. |
| 2016/0283900 A1 | 9/2016 | Johnson et al. |
| 2017/0014073 A1 | 1/2017 | Shoshani et al. |
| 2017/0027469 A1 | 2/2017 | Amir et al. |
| 2017/0036066 A1 | 2/2017 | Chahine |
| 2017/0040758 A1 | 2/2017 | Amir et al. |
| 2017/0162840 A1 | 6/2017 | Pendry |
| 2017/0319862 A1 | 11/2017 | Foshee, Jr. et al. |
| 2017/0367591 A1 | 12/2017 | Jorgenson |
| 2018/0116537 A1 | 5/2018 | Sullivan et al. |
| 2018/0117299 A1 | 5/2018 | Gustavson et al. |
| 2018/0184933 A1 | 7/2018 | Sullivan et al. |
| 2018/0185662 A1 | 7/2018 | Foshee, Jr. et al. |
| 2018/0243578 A1 | 8/2018 | Volosin |
| 2018/0361165 A1 | 12/2018 | Jaax et al. |
| 2019/0030352 A1 | 1/2019 | Sullivan et al. |
| 2019/0076666 A1 | 3/2019 | Medema |
| 2019/0116896 A1 | 4/2019 | Armour et al. |
| 2019/0321650 A1 | 10/2019 | Raymond et al. |
| 2020/0155826 A1 | 5/2020 | Kaib et al. |

FOREIGN PATENT DOCUMENTS

| | | |
|---|---|---|
| JP | 4320257 B2 | 8/2009 |
| JP | 2014526282 A | 10/2014 |
| JP | 5963767 B2 | 8/2016 |
| WO | 1998039061 A2 | 9/1998 |
| WO | 2011146448 A1 | 11/2011 |
| WO | 2012064604 A1 | 5/2012 |
| WO | 2012151160 A1 | 11/2012 |
| WO | 2015056262 A1 | 4/2015 |

OTHER PUBLICATIONS

LIFECOR LifeVest System Model WCD 3100 Operator's Manual, 2006, ZOLL Lifecor Corporation, Pittsburgh, PA, PN 20B0040 Rev FI, 48 pages.

LifeVest Model 4000 Patient Manual, 108 pages, ZOLL, Pittsburgh, PA, PN 20B0047 Rev B.

Heartstart MRx and XL AED Algorithm—Application Note, Jul. 2001, Edition 2, Philips Healthcare, USA.

The LifeVest Network/Patient Data Management System, Zoll, 2015, 2000503 Rev A.

Pagan-Carlo, L.A., et al., "Encircling Overlapping Multipulse Shock Waveforms for Transthoracic Defibrillation," JACC Journals 32(7)12065-2071, Dec. 1998.

Zoll, LifeVest, Proven protection from Sudden Cardiac Death, issued Mar. 27, 2018, 4 pages. Pittsburgh PA, USA.

International Search Report and Written Opinion dated May 20, 2016, issued in International Application No. PCT/US2015/051726, filed Sep. 23, 2015, 10 pages.

\* cited by examiner

SAMPLE COMPONENTS OF EXTERNAL DEFIBRILLATOR

WEARABLE CARDIOVERTER DEFIBRILLATOR HAVING REDUCED NOISE PROMPTS

CROSS REFERENCE TO RELATED PATENT APPLICATIONS

This patent application claims benefit of U.S. Provisional Patent Application No. 62/442,919 filed Jan. 5, 2017, titled WCD WITH REDUCED NOISE PROMPT, which is incorporated by reference herein in its entirety.

BACKGROUND

When people suffer from some types of arrhythmias, the results may be that blood flow to various parts of the body is reduced, and some arrhythmias may even result in sudden cardiac arrest (SCA), which can lead to death very quickly unless treated immediately.

People with an increased risk of SCA often receive an implantable cardioverter defibrillator (ICD). If certain types of heart arrhythmias are detected, then the ICD delivers an electric shock through the heart. However, prior to receiving the ICD, many of these patients receive a wearable cardioverter defibrillator (WCD) system. A WCD system typically includes a harness, vest, or other garment that the patient wears, as well as electronic components, such as a defibrillator and external electrodes, coupled to the garment. When the patient wears the WCD system, the external electrodes make electrical contact with the patients skin to help determine the patient's electrocardiogram (ECG). If a shockable heart arrhythmia is detected, the defibrillator may then deliver an appropriate shock through the patient's body.

However, the electrodes may fail to make a good electrical connection with the patient's skin, which may create artifacts, also referred to herein as noise, in the ECG signal that is detected. Noise on the ECG signal may interfere with a rhythm analysis to determine if a shock is needed by a patient. Accordingly, many WCD systems include a noise detection to prompt the patient when noise is present to adjust the WCD garment or electrodes to stop the noise if possible. Noise prompts, however, may be disturbing to the patient since they require the patient's attention and may wake the patient during sleep or require the patient to adjust their clothing in a public location.

This disclosure addresses these and other deficiencies of the prior art.

BRIEF DESCRIPTION OF THE DRAWINGS

Aspects, features and advantages of embodiments of the present disclosure will become apparent from the following description of embodiments in reference to the appended drawings in which.

DESCRIPTION

In general, embodiments of the disclosure relate to a wearable cardioverter defibrillator (WCD) including a support structure configured to be worn by an ambulatory patient, an energy storage module configured to store an electrical charge, a discharge circuit coupled to the energy storage module, electrodes configured to render an electrocardiogram (ECG) signal of the patient while the patient is wearing the support structure, a user interface configured to output an alarm in response to a noise alarm signal, and a processor. The processor is configured to receive the ECG signal, determine whether noise is present on the ECG signal, determine from the ECG signal whether a shock criterion is met, and cause the user interface to generate the noise alarm signal when the noise is present on the ECG signal and the shock criterion is met and not generate the noise alarm signal when noise is present on the ECG signal and the shock criterion is not met. In some embodiment, the WCD may treat high frequency noise and high amplitude noise differently. For example, high amplitude noise may cause the WCD to suspend analysis of the ECG signal until the high amplitude noise is corrected.

A WCD system made according to embodiments has a number of components. These components can be provided separately as modules that can be interconnected, or can be combined with other components, etc.

Figure 1:
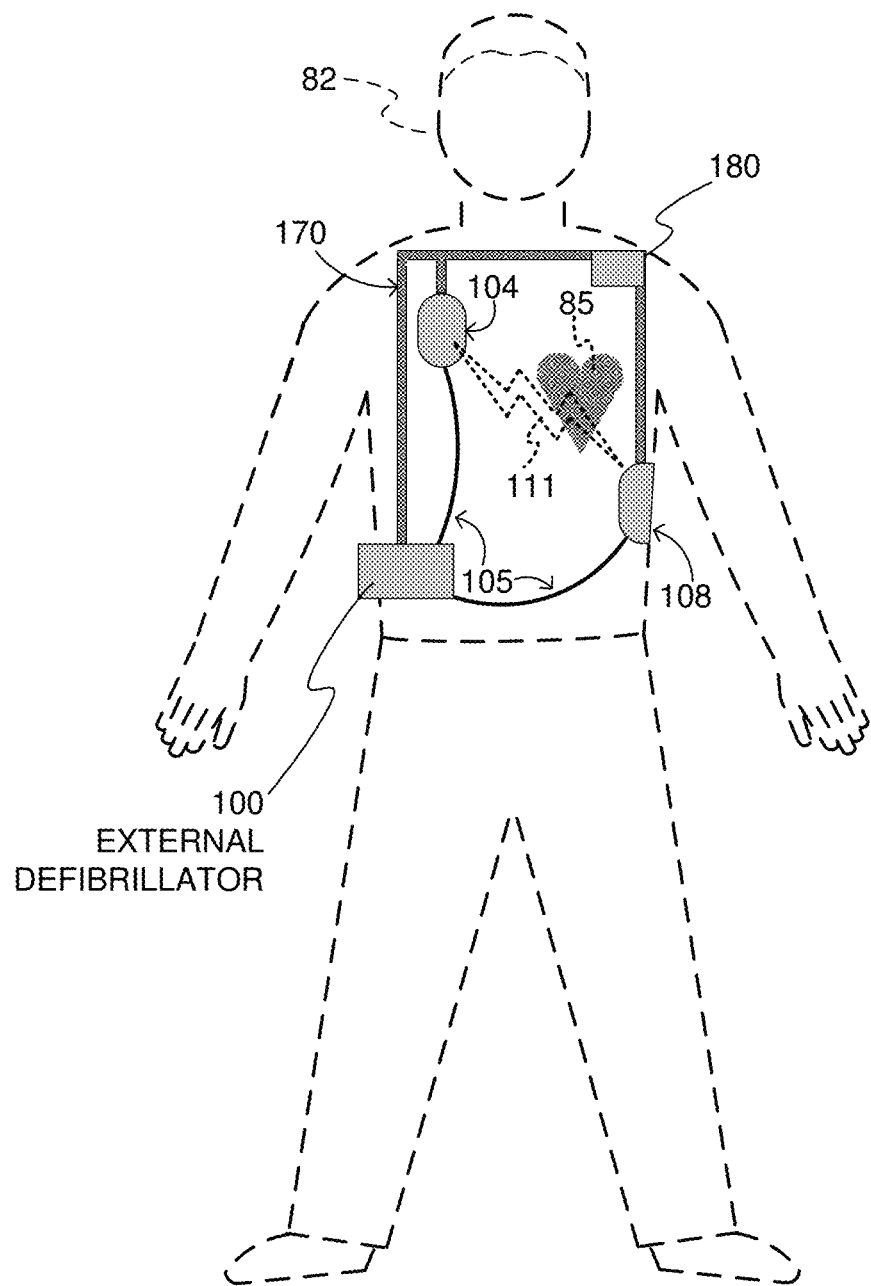
FIG. 1 is a diagram of components of a sample WCD system, according to embodiments of the disclosure.

FIG. 1 depicts a patient 82. Patient 82 may also be referred to as a person and/or wearer, since that patient wears components of the WCD system. Patient 82 is ambulatory, which means patient 82 can walk around and is not bedridden.

FIG. 1 also depicts components of a WCD system made according to embodiments disclosed herein. One such component is a support structure 170 that is wearable by patient 82. It will be understood that support structure 170 is shown only generically in FIG. 1. FIG. 1 is provided merely to illustrate concepts about support structure 170, and is not to be construed as limiting how support structure 170 is implemented or worn.

Support structure 170 can be implemented in many different ways. For example, it can be implemented in a single component or a combination of multiple components. In some embodiments, support structure 170 could include a vest, a half-vest, a garment, etc. Such items can be worn similarly to parallel articles of clothing. In some embodiments, support structure 170 could include a harness, one or more belts or straps, etc. Such items can be worn by the patient around the torso, hips, over the shoulder, etc. In embodiments, support structure 170 can include a container or housing, which can even be waterproof. In some embodiments, the support structure can be worn by being attached to the patient by adhesive material. Of course, in some embodiments, a person skilled in the art will recognize that additional components of the WCD system can be in the housing of a support structure instead of attached externally to the support structure.

A WCD system according to embodiments disclosed herein is configured to defibrillate a patient who is wearing it, by delivering an electrical charge to the patient's body in the form of an electric shock delivered in one or more pulses. FIG. 1 shows a sample external defibrillator 100, and sample defibrillation electrodes 104, 108, which are coupled to external defibrillator 100 via electrode leads 105. Defibrillator 100 and defibrillation electrodes 104, 108 can be coupled to support structure 170. As such, many of the components of defibrillator 100 could be therefore coupled to support structure 170. When defibrillation electrodes 104, 108 make good electrical contact with the body of patient 82, defibrillator 100 can administer, via electrodes 104, 108, a brief, strong electric pulse 111 through the body. Pulse 111, also known as shock, defibrillation shock, therapy or therapy shock, is intended to go through and restart heart 85, in an effort to save the life of patient 82. Pulse 111 can further include one or more pacing pulses, and so on.

A conventional defibrillator typically decides whether to defibrillate or not based on an ECG signal of the patient. However, external defibrillator 100 may initiate defibrillation (or hold-off defibrillation) based on a variety of inputs, with ECG merely being one of them.

Accordingly, it will be appreciated that signals such as physiological signals containing physiological data are obtained from patient 82. While the patient may be considered also a "user" of the WCD system, this is not a requirement. That is, for example, a user of the wearable cardioverter defibrillator (WCD) may include a clinician such as a doctor, nurse, emergency medical technician (EMT) or other similarly situated individual (or group of individuals). The particular context of these and other related terms within this description should be interpreted accordingly.

The WCD system may optionally include an outside monitoring device 180. Device 180 is called an "outside" device because it could be provided as a standalone device, for example, not within the housing of defibrillator 100. Device 180 can be configured to sense or monitor at least one local parameter. A local parameter can be a parameter of patient 82, or a parameter of the WCD system, or a parameter of the environment. Device 180 may include one or more transducers or sensors that are configured to render one or more physiological inputs from one or more patient parameters that it senses.

Optionally, device 180 is physically coupled to support structure 170. In addition, device 180 can be communicatively coupled with other components, which are coupled to support structure 170. Such communication can be implemented by a communication module, as will be deemed applicable by a person skilled in the art in view of this disclosure.

Figure 2:
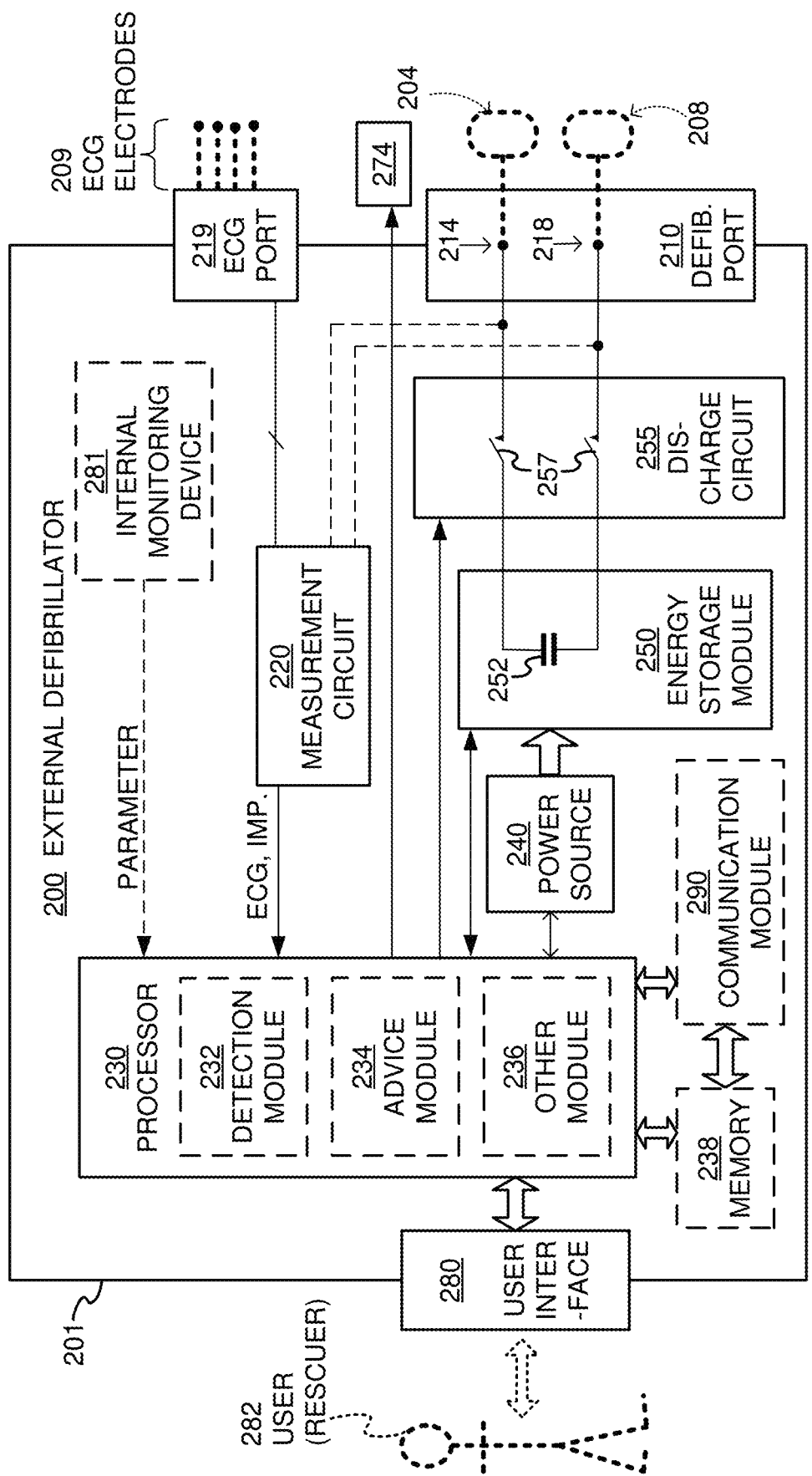
FIG. 2 is a block diagram illustrating sample components of an external defibrillator, such as the one belonging in the system of FIG. 1, according to embodiments of the disclosure.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as patient 82 of FIG. 1. Defibrillator 200 may further include a user interface 280 for a user 282. User 282 can be patient 82, also known as wearer 82. Or user 282 can be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible or tactile, for communicating to a user by outputting images, sounds or vibrations. Images, sounds, vibrations, and anything that can be perceived by user 282 can also be called human perceptible indications. There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds to warn bystanders, etc.

User interface 280 may further include input devices for receiving inputs from users. Such input devices may additionally include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which monitoring device can be done according to design considerations. Device 281 may include one or more transducers or sensors that are configured to render one or more physiological inputs from one or more patient parameters that it senses.

Patient parameters may include patient physiological parameters. Patient physiological parameters may include, for example and without limitation, those physiological parameters that can be of any help in detecting by the wearable defibrillation system whether the patient is in need of a shock, plus optionally their medical history and/or event history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an Sp02 sensor, and so on. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection. In such cases, the transducer includes an appropriate sensor, and the physiological input is a measurement by the sensor of that patient parameter. For example, the appropriate sensor for a heart sound may include a microphone, etc.

In some embodiments, the local parameter is a trend that can be detected in a monitored physiological parameter of patient 282. A trend can be detected by comparing values of parameters at different times. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from Sp02 or C02; f) respiratory function, respiratory rate, etc.; g) motion, level of activity; and so on. Once a trend is detected, it can be stored and/or reported via a communication link, along perhaps with a warning. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may include a motion detector. In embodiments, a motion detector can be implemented within monitoring device 180 or monitoring device 281. Such a motion detector can be configured to detect a motion event. In response, the motion detector may render or generate from the detected motion event a motion detection input that can be received by a subsequent device or functionality. A motion event can be defined as is convenient, for example a change in motion from a baseline motion or rest, etc. Such a motion detector can be made in many ways as is known in the art, for example by using an accelerometer. In such cases, the patient parameter is a motion, one of the transducers may include a motion detector, and the physiological input is a motion measurement.

System parameters of a WCD system can include system identification, battery status, system date and time, reports of self-testing, records of data entered, records of episodes and intervention, and so on.

Environmental parameters can include ambient temperature and pressure. Moreover, a humidity sensor may provide information as to whether it is likely raining. Presumed patient location could also be considered an environmental parameter. The patient location could be presumed if monitoring device 180 or 281 includes a GPS location sensor as per the above.

Defibrillator 200 typically includes a defibrillation port 210, such as a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in an energy storage module 250 that is described more fully later in this document. The electric charge will be the shock for defibrillation, pacing, and so on.

Defibrillator 200 may optionally also have an ECG port 219 in housing 201, for plugging in sensing electrodes 209, which are also known as ECG electrodes and ECG leads. It is also possible that sensing electrodes 209 can be connected continuously to ECG port 219, instead. Sensing electrodes 209 are types of transducers that can help sense an ECG signal, e.g. a 12-lead signal, or a signal from a different number of leads, especially if they make good electrical contact with the body of the patient. Sensing electrodes 209 can be attached to the inside of support structure 170 for making good electrical contact with the patient, similarly as defibrillation electrodes 204, 208.

Optionally a WCD system according to embodiments also includes a fluid that it can deploy automatically between the electrodes and the patient's skin. The fluid can be conductive, such as by including an electrolyte, for making a better electrical contact between the electrode and the skin. Electrically speaking, when the fluid is deployed, the electrical impedance between the electrode and the skin is reduced. Mechanically speaking, the fluid may be in the form of a low-viscosity gel, so that it does not flow away, after it has been deployed. The fluid can be used for both defibrillation electrodes 204, 208, and sensing electrodes 209.

The fluid may be initially stored in a fluid reservoir, not shown in FIG. 2, which can be coupled to the support structure. In addition, a WCD system according to embodiments further includes a fluid deploying mechanism 274. Fluid deploying mechanism 274 can be configured to cause at least some of the fluid to be released from the reservoir, and be deployed near one or both of the patient locations, to which the electrodes are configured to be attached to the patient. In some embodiments, fluid deploying mechanism 274 is activated prior to the electrical discharge responsive to receiving activation signal (AS) from processor 230.

In some embodiments, defibrillator 200 also includes a measurement circuit 220, as one or more of its sensors or transducers. Measurement circuit 220 senses one or more electrical physiological signals of the patient from ECG port 219, if provided. Even if defibrillator 200 lacks ECG port 219, measurement circuit 220 can obtain physiological signals through nodes 214, 218 instead, when defibrillation electrodes 204, 208 are attached to the patient. In these cases, the physiological input reflects an ECG measurement. The parameter can be an ECG, which can be sensed as a voltage difference between electrodes 204, 208. In addition, the parameter can be an impedance, which can be sensed between electrodes 204, 208 and/or the connections of ECG port 219. Sensing the impedance can be useful for detecting, among other things, whether these electrodes 204, 208 and/or sensing electrodes 209 are not making good electrical contact with the patient's body. These patient physiological signals can be sensed, when available. Measurement circuit 220 can then render or generate information about them as physiological inputs, data, other signals, etc. More strictly speaking, the information rendered by measurement circuit 220 is output from it, but this information can be called an input because it is received by a subsequent device or functionality as an input.

Defibrillator 200 also includes a processor 230. Processor 230 may be implemented in a number of ways. Such ways include, by way of example and not of limitation, digital and/or analog processors such as microprocessors and Digital Signal Processors (DSPs); controllers such as microcontrollers; software running in a machine; programmable circuits such as Field Programmable Gate Arrays (FPGAs), Field Programmable Analog Arrays (FPAAs), Programmable Logic Devices (PLDs), Application Specific Integrated Circuits (ASICs), any combination of one or more of these, and so on.

The processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions generally provide functionality by performing methods as may be disclosed herein or understood by one skilled in the art in view of the disclosed embodiments. In some embodiments, and as a matter of convention used herein, instances of the instructions may be referred to as a "module" and by other similar terms. Generally, a module includes a set of the instructions so as to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as physiological inputs, data, or other signals, may be used by the VF detector to determine whether the patient is experiencing VF. Detecting VF is useful, because VF results in SCA. Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments, and determining whether a shock criterion is met. The determination can be made from a rhythm analysis of the captured ECG signal or otherwise.

In some embodiments, when the determination is to shock, an electrical charge is delivered to the patient. Delivering the electrical charge is also known as discharging. Shocking can be for defibrillation, pacing, and so on.

Processor 230 can include additional modules, such as other module 236, for other functions. In addition, if internal monitoring device 281 is indeed provided, it may be operated in part by processor 230, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, actions and/or methods to be performed, and/or the processor to cause other devices or components or blocks to perform such functions, operations, processes, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or stored there after it is received by defibrillator 200.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy storage capacitor, and so on. In some embodiments, power source 240 is controlled by processor 230. Appropriate components may be included to provide for charging or replacing power source 240.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

Defibrillator 200 moreover includes a discharge circuit 255. When the decision is to shock, processor 230 can be configured to control discharge circuit 255 to discharge through the patient the electrical charge stored in energy storage module 250. When so controlled, circuit 255 can permit the energy stored in module 250 to be discharged to nodes 214, 218, and from there also to defibrillation electrodes 204, 208, so as to cause a shock to be delivered to the patient. Circuit 255 can include one or more switches 257. Switches 257 can be made in a number of ways, such as by an H-bridge, and so on. Circuit 255 can also be controlled via user interface 280.

Defibrillator 200 can optionally include a communication module 290, for establishing one or more wired or wireless communication links with other devices of other entities, such as a remote assistance center, Emergency Medical Services (EMS), and so on. Module 290 may also include such sub-components as may be deemed necessary by a person skilled in the art, for example an antenna, portions of a processor, supporting electronics, outlet for a telephone or a network cable, etc. This way, data, commands, etc. can be communicated. The data can include patient data, event information, therapy attempted, CPR performance, system data, environmental data, and so on.

Defibrillator 200 can optionally include other components.

Returning to FIG. 1, in embodiments, one or more of the components of the shown WCD system have been customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. Such baseline physiological parameters can be used to customize the WCD system, in order to make its diagnoses more accurate, since the patients' bodies differ from one another. Of course, such parameters can be stored in a memory of the WCD system, and so on.

A programming interface can be made according to embodiments, which receives such measured baseline physiological parameters. Such a programming interface may input automatically in the WCD system the baseline physiological parameters, along with other data.

As mentioned above, electrodes 209, or even electrodes 204 & 208 can be configured to render an electrocardiogram (ECG) signal of the patient, while the patient is wearing the support structure.

Because a WCD system is worn by ambulatory patients, noise on the ECG signal generated at the electrode-skin interface can create a significant problem, as mentioned above. That is, patient movement may generate noise that can interfere with analysis of the ECG signal. If the noise level is high enough on the ECG signal to interfere with rhythm interpretation, then the patient may need to be alerted to take corrective action. Depending on the situation, the noise may be eliminated by correcting a problem with the WCD garment or by discontinuing the activity that is generating the noise.

As mentioned above, noise alerts may be bothersome for the patient and require a patient's attention to take corrective action and/or divert therapy. Noise alerts, however, serve an important function and alert the patient to respond. Sometimes the patient may respond by stopping their activity or adjusting a garment. If, for example, the garment is too loose, the garment may produce more noise that could lead to more false shock alarms and more inappropriate shocks. By alerting the patient of the need to correct the noise, the patient may be spared the more disturbing trauma of unnecessary shock alarms and shocks. A patient may silence a noise alert by, for example, pressing a button the WCD system. However, excessive alerts are bothersome. As such, a WCD that is noise tolerant and that can discriminate between noise that may interfere with a rhythm analysis and noise that a rhythm analysis algorithm will tolerate may be beneficial to the patient. Embodiments of the disclosure only trigger a patient alert for noise that interferes with rhythm analysis so that a patient is not alerted for every detected noise.

As mentioned above, the processor 230, through the detection module 232 and the advice module 234, performs a rhythm analysis to decide when a patient should receive a shock. In some embodiments, the rhythm analysis uses heart rate, QRS width, and QRS organization from the ECG data to make a shock decision, as shown in Table 1 below:

TABLE 1

| Parameter | No Shock | VT | VF | VF |
|---|---|---|---|---|
| Heart Rate | <170 BPM | >170 BPM | >200 BPM | >200 BPM |
| QRS Width | Don't care | >80 ms | >80 ms | >80 ms |
| Organization | Don't care | High | Low | Don't care |
| Confirmation Time | N/A | Long | Short | Short |

The rhythm analysis distinguishes between VT and VF because it is often desirable to shock a patient quickly if VF is detected, but take more time before shocking for VT because may self-terminate.

There are multiple ways to identify noise on the ECG signal from the measurement circuit 220. The processor 230 determines the activity of heart 85 at least from the ECG signal, which may include identifying QRS complexes within the ECG to compute the patient's heart rate.

For example, depending on a monitoring level of a lead vector, QRS complexes may vary in amplitude. Typically, QRS complexes do not have an amplitude greater than 1.5 mV-4 mV. QRS amplitudes may vary with lead location, so different thresholds may be used for different WCD systems, as well. QRS amplitudes are typically measured with a signal that has been high pass filtered, so it may be assumed the baseline is near zero. The amplitude of a detection point is then the QRS amplitude. Allowing some margin of error, an amplitude threshold may be set, for example, of approximately 5 mV to determine noise. Any amplitude over 5 mV on the QRS complex is flagged as noise, and not a QRS complex, since QRS complexes should be less than 4 mV. Although the amplitude threshold example here is 5 mV, any amplitude threshold may be used that indicates that a QRS complex is actually detected noise. The amplitude threshold, however, may between 2-20 mV, for example, depending on the WCD system and the lead location.

The threshold for noise may also be adjusted for a particular patient. For example, if a patient's QRS complexes are normally 1 mV, a detection with a 2 mV peak may be considered noise. Noise thresholds can be set by a clinician when the WCD is first prescribed, or they may be set automatically by the device. For a device that monitors multiple ECG channels, the thresholds may be different for different channels since QRS amplitudes may be different.

Noise may also be determined by a baseline shift in the ECG signal. While the ECG signal must be high pass filtered before analysis, the act of filtering may cause important information that indicates a noisy signal to be lost. That is, when viewing a filtered signal, a shift in the signal baseline may appear as a narrow blip that could be a QRS complex. However, a baseline shift may be detected by looking at the unfiltered ECG signal. If the unfiltered ECG signal changes in amplitude by more than approximately 5 mV in the vicinity of a QRS detection, it is likely the QRS detection is actually related to noise. As such, after a QRS complex is detected, processor 230 may look at the unfiltered ECG signal and compare it to an amplitude threshold of 5 mV, for example, to determine if the change in amplitude in the vicinity of the detected QRS complex is greater than the amplitude threshold. If then change in amplitude is greater than the amplitude threshold, the detected QRS complex is flagged as noise. The amplitude threshold, however, may between 2-20 mV, for example, depending on the WCD system and the lead location.

Both the QRS amplitude detection and baseline shift noise detection may be characterized and flagged as high amplitude noise. High amplitude noise may often be caused by patient motion that causes an electrode 204, 208, or 209 to shift to a new position on the skin of the patient.

Other types of noise detection may be characterized and flagged as high frequency noise. For example, high frequency artifacts commonly show up on ECG signals. These artifacts can be caused by electrical interference, such as 60 Hz power, or by skeletal muscle artifacts. In some embodiments, high frequency artifacts may be detected by counting the number of times the ECG signal crosses zero, i.e., the baseline. Cardiac ECG signals have a limited number of zero, or baseline, crossings in the vicinity of a QRS complex. Normal complexes are not near the baseline during a QRS complex, and VF has a frequency content of up to about 8 Hz. In both cases, the number of zero crossings in the vicinity of the detection point is limited. If a window is defined at 180 ms after a detection point, normal signals will have fewer than five zero crossings. Accordingly, a threshold may be set to flag the ECG signal as noisy if more than five zero crossings are present within 180 ms after detecting a QRS complex.

Further, normal QRS complexes have a width of at least approximately 20 ms. Any peaks narrower than 20 ms are most likely due to noise. Narrow peaks may be caused by high frequency artifacts, such as 60 Hz noise or from an implanted device, such as a pacemaker. Processor 230 may flag the ECG signal as having high frequency noise when a peak is narrower than 20 ms. That is, a peak threshold may be set at 20 ms and any peak narrower than 20 ms is characterized and flagged as noise.

As mentioned above, noise detected by the baseline crossings and the narrow peak may be classified as high frequency noise by the processor 230, which may be treated differently in some embodiments from high amplitude noise, as discussed in more detail below.

The processor 230 may also determine noise in some embodiments by detecting a correlation between a channel receiving the ECG signal and a physical sensor, such as an accelerometer, signal, a leads-off signal (for the given channel or a different channel), an impedance signal, or a common-mode voltage. Since these signals are not expected to pick up QRS complexes, a correlation to the ECG signal mostly likely means that the ECG channel is corrupted with noise. In some embodiments, the correlation is measured in terms of cross-correlation between signals, by comparing the dominant frequency of a fast fourier transform (FFT), by counting zero crossings, or by counting peaks. The processor 230 flags the ECG channel as having noise when there is a high correlation with any of these signals. This channel may then be ignored for analysis or the whole ECG signal may be flagged as noisy.

In some embodiments, if an excessive number of beats is detected on an ECG channel connected to an electrode, then that channel and electrode may be disqualified from use in calculating heart rate and QRS width, until the noise clears. If the noise lasts for an extended period of time, then the patient may be alerted to take action to clear the noise.

Noise may also be determined by the processor 230 when a high rate of change on a physical sensor is coincident with a QRS complex detection. Since physical sensors are not expected to be correlated to cardiac signals, a disturbance that causes a transient on a physical sensor may show up as an artifact on the ECG signal. If a QRS complex is detected and it happens there is a transient on another sensor, then it is likely that the QRS complex is a false detection and is flagged as noise by the processor 230.

Noise may also be determined in additional ways on the ECG signal, as would be understood by one skilled in the art. That is, embodiments disclosed herein are not limited to the noise detections discussed above. Further, the processor 230 may determine noise on the ECG signal in segments. That is, the ECG signal may be broken up into a plurality of segments, each segment including a time period of ECG signal, for example. The time period may be any desired time period, such as 4.8 seconds. Alternatively, the processor 230 may determine noise by applying the above-discussed thresholds to a QRS complex detected by a QRS detector, with a detected complex labeled as noise. If labeled as noise, the QRS complex could be rejected and not used for heart rate calculations, avoiding a possible disturbance to the heart rate. In some embodiments, if too many complexes are rejected, then an ECG channel may be labeled as noisy and a patient may be alerted of the noise.

The noise detection processes discussed above may be applied to WCD systems that processor QRS complexes continuously as well as those that process the data in segments.

Figure 3:
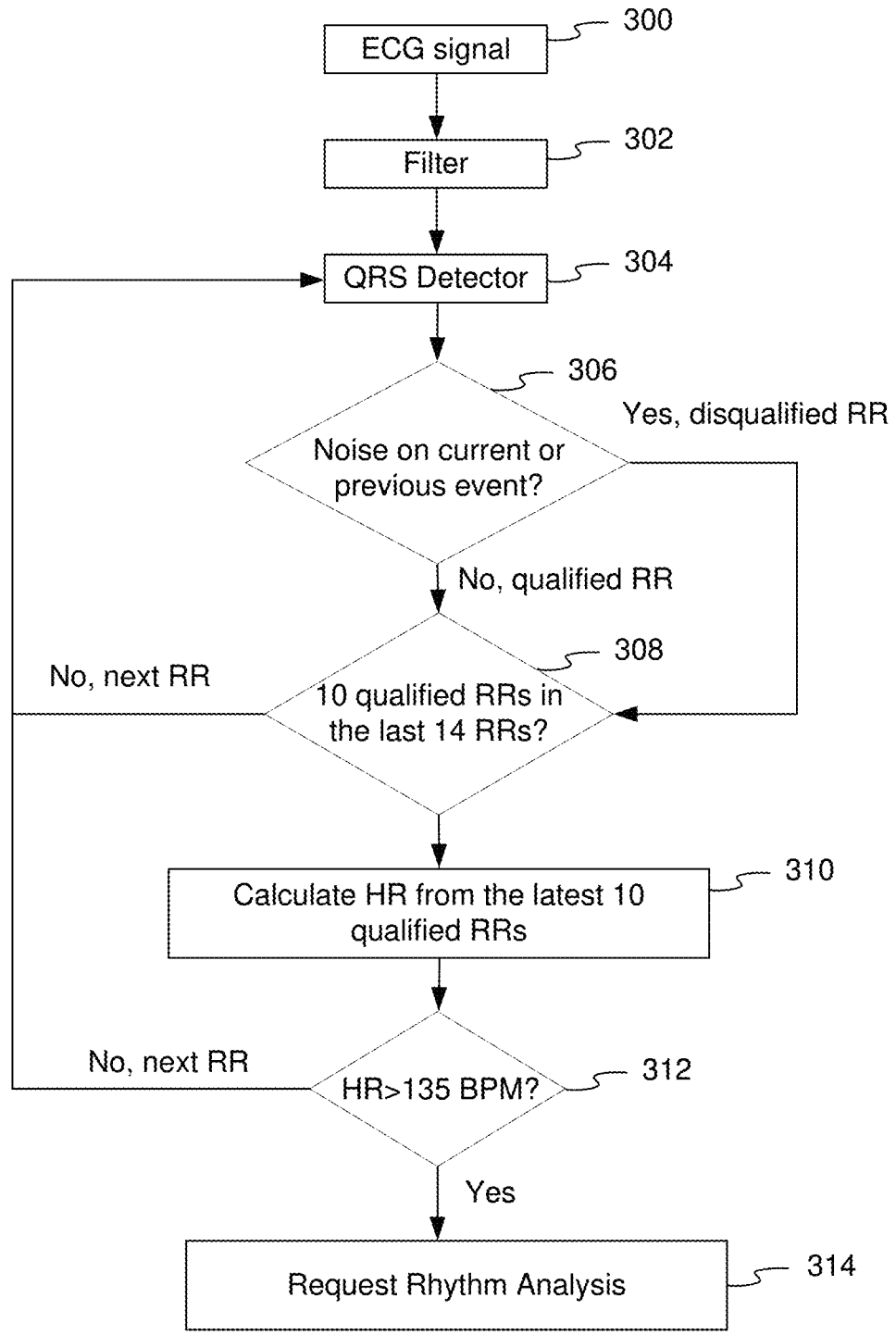
FIG. 3 is a flow chart illustrating an example process of incorporating noise detection into a QRS detection to ignore complexes that are detected as noise.

FIG. 3 illustrates an example process of incorporating noise detection into a QRS detection to ignore complexes that are detected as noise. False QRS complex detections can alter the heart rate and QRS width measurements made on false detections will likely yield an incorrect width. As shown in FIG. 3, in some embodiments, rhythm analysis is inhibited on noisy segments of the ECG signal. This approach precludes the possibility of noise leading to a wrong rhythm analysis result. However, in this situation, a user may be alerted with a noise alarm each time noise is present. If a patient does not respond to the noise alarm, the processor 230 may assume the patient needs to be shocked and would begin a shock sequence.

Initially, at operation 300, ECG data from one of the electrodes 204, 208, and 209. In operation 302, the ECG signal is filtered and then in operation 304, the processor 230 detects any QRS complexes within the filtered ECG signal. In operation 306, the processor 230 determines whether noise is present on the currently detected QRS complex or a previous QRS complex. If yes, the event inter-beat (RR) interval, or event, is disqualified. If no, then in operation 308, the processor 230 determines whether there have been ten qualified RR intervals in the last fourteen RR intervals. If not, then the process returns to operation 304. If yes, then the heart rate of the patient is calculated using the ten qualified RR intervals in operation 310. In operation 312, it is determined if the heart rate is greater than 135 beats per minute (BPM). If no, then the process returns to operation 304. If yes, then rhythm analysis is requested to determine whether a shock is recommended.

Precluding a rhythm analysis any time noise is present may require a device to give more noise alerts to a patient than necessary. Most of the time noise is caused by patient movement, and a patient moving is probably not in cardiac arrest. Typically, noise on an ECG signal is an indication itself that a patient does not need to be shocked.

The effect of noise on the ECG signal in rhythm analysis is not random and is more likely to make a non-shockable rhythm look like VT/VF (a false positive) than to make VT/VF look like a non-shockable rhythm (a false negative). This is particularly true if noise persists long enough that it interferes with device performance. False positives tend to happen from persistent activities, like walking, while false negatives tend to happen from one-time transients, like sitting in a chair quickly. A one-time transient may interfere with a single rhythm analysis, but because the WCD system continually analyzes the ECG signal, the error would be corrected on the next rhythm analysis. Persistent transients are more problematic as they may last long enough for the WCD system to conclude that a shock is necessary.

Conventional WCD systems treat all noise detected on the ECG signal the same and output a noise alert when noise is present and begin a shock response if a user input is not received within a predetermined amount of time. As a result, conventional WCD systems may give many more noise alerts than are necessary.

Some embodiments of this disclosure reduce unnecessary noise prompts, or outputs, even when running a rhythm analysis regardless of whether noise is detected. However, in some embodiments a noise alert is only generated by the processor 230 when both noise is detected and a shock is recommended from the rhythm analysis. Noise may be ignored if the rhythm analysis determines that a shock is not required, as shown in Table 2 below:

TABLE 2

| Noise Detected | Rhythm Analysis Result | Device Behavior |
|---|---|---|
| Noise | Shock | Noise alert, shock if no response |
| Noise | No Shock | No alert, no shock |
| No Noise | Shock | Shock |
| No Noise | No Shock | No Shock |

Figure 4:
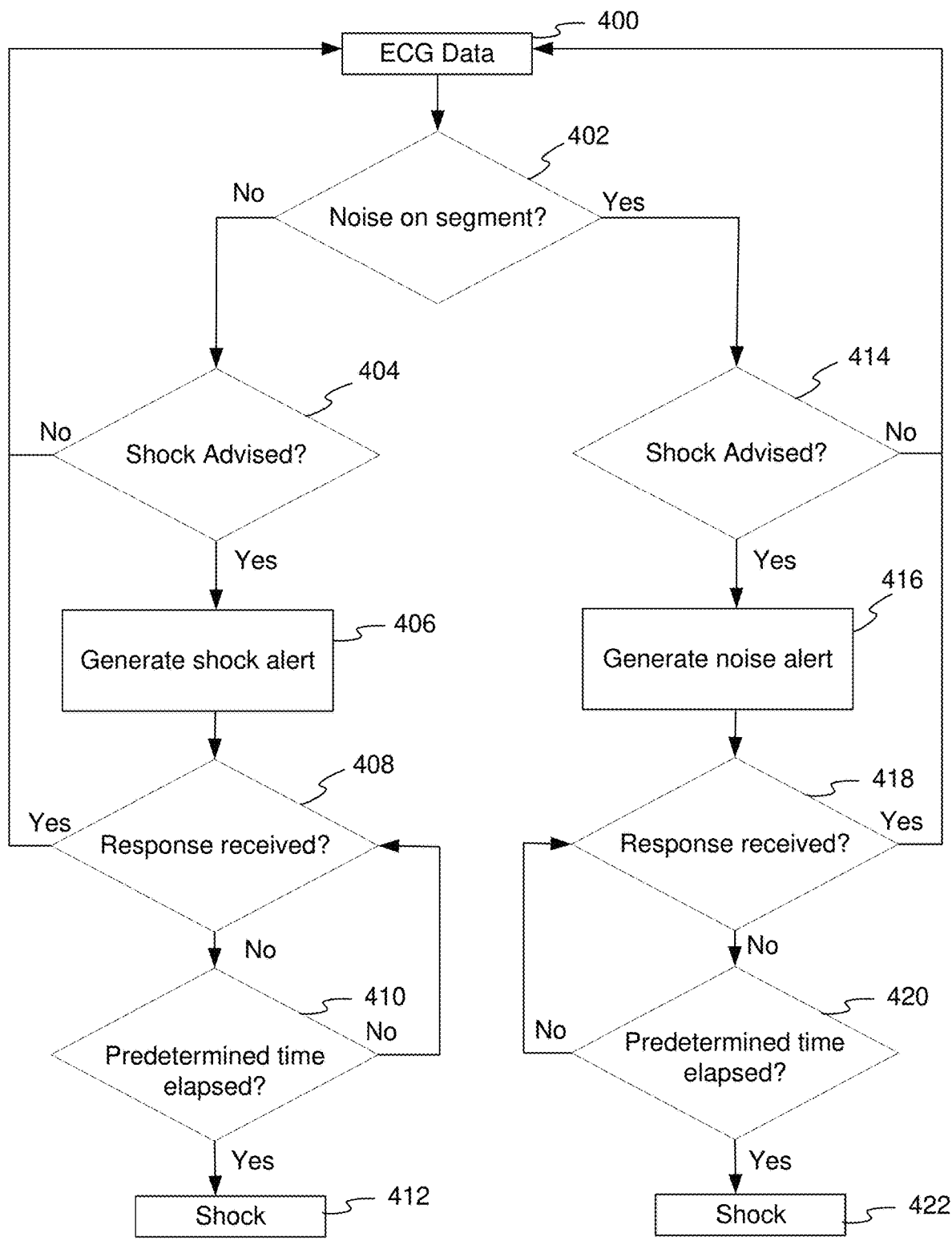
FIG. 4 is a flow chart illustrating an example process of alerting a patient when noise is detected on an ECG signal.

FIG. 4 illustrates this embodiment of the disclosure. In FIG. 4, ECG signal is received and analyzed at operation 400 and in operation 402, processor 230 determines if noise is present on the signal. If noise is not present, operation 404 determines if a shock is advised. If not, then the process returns to operation 400. If operation 404 determines a shock is advised, then a shock alert is generated in operation 406 to warn the patient and any bystanders that a shock is going to occur. In operation 408, if a response is received by the user at the user interface 270, then the WCD does not shock the patient and the processor 230 returns to operation 400. If a response has not been received at 408, the process determines if a predetermined amount of time has elapsed in operation 410. The predetermined amount of time may be set by the processor 230 based on the type of arrhythmia detected on the ECG data 400. For example, if the arrhythmia is VT, the system may wait for a longer period of time for a user input than if the arrhythmia is VF. If the predetermined time has elapsed and no response has been received by the user to divert the shock, then the processor 230 controls the discharge circuit 255 to discharge the stored electrical charge and shock the patient in operation 412.

If noise is determined in operation 402 to be present on the ECG data, in operation 414, the process determines if a shock is advised. If no, the processor 230 returns to operation 400. If yes, a noise alert is generated in operation 416, and similar to operations 408, 410 and 412, in operation 418 it is determined if a response is received and if yes, the shock is diverted. If no, then the process determines if a predetermined amount of time has elapsed in operation 420. If the predetermined amount of time has not elapsed, then the process returns to determining if a response has been received in operation 418. If yes, then a shock is given to a patient in operation 422. This allows the processor 230 to confirm if a shock should be given or if the patient has responded and the shock is diverted.

Figure 5:
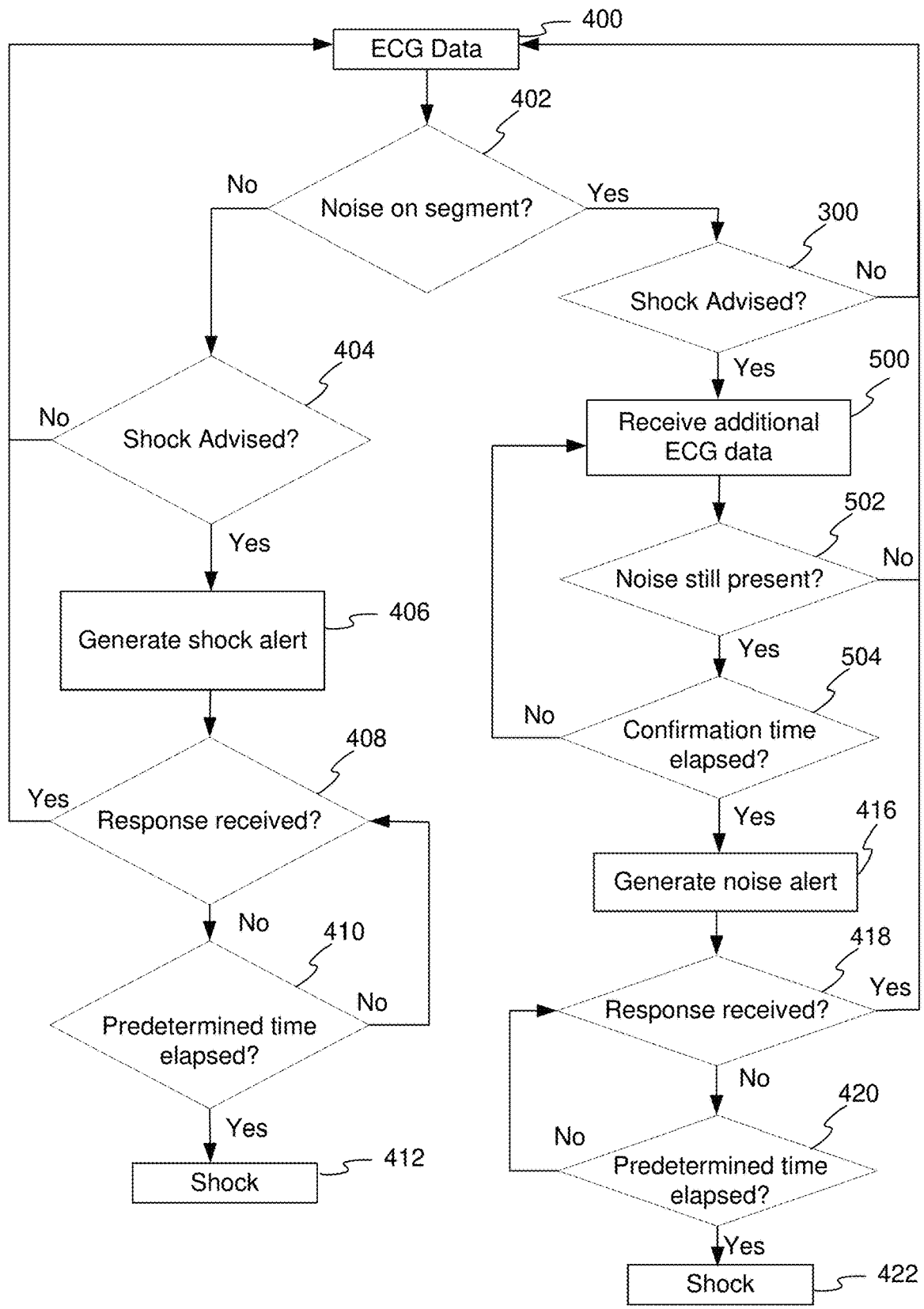
FIG. 5 is a flow chart illustrating another example process of alerting a patient when noise is detected on an ECG signal.

FIG. 5 illustrates an alternative embodiment to that of FIG. 4 which waits for a confirmation time to determine if the noise clears up on its own prior to generating a shock alert to a patient. The embodiment shown in FIG. 4 may also include a confirmation time, as would be understood by one skilled in the art. In FIG. 5, operations 402-414 remain the same, and as such are not discussed in further detail here. However, after it is determined a shock is advised in operation 414, then the process receives additional ECG signal in operation 500 to determine if noise is still present on the ECG signal. Accordingly, in this embodiment, rather than generating the noise alert and extending the response time, the confirmation is done prior to generating the noise alert. Accordingly, after additional ECG signal is received in operation 500, the process determines if noise is present on the additional ECG signal in operation 502. If no, then the process returns to operation 400. If yes, then the process determines in operation 504 if a predetermined time has elapsed. The predetermined time may be, for example, between five seconds and fifteen minutes, depending on the type of arrhythmia detected. If not, then the process returns to operation 500 to receive additional ECG data. If yes, then the noise alert is generated as in operation 416, and the process proceeds the same as in FIG. 4.

FIG. 5 allows time for the noise to self-terminate prior to generating the shock alert to the patient. In this embodiment, the confirmation time may also be extended or may be the same confirmation time as if no noise was present.

The confirmation may be longer for VT, such as 45 seconds, and shorter for VF, which may be 15 seconds. However, since most noise is generated by patient motion, and patients in cardiac arrest are not expected to be moving, in some embodiments, the confirmation time may be extended even more when noise is detected in the ECG signal. That is, whether VT or VF is detected, the confirmation time may be between forty-five seconds to a minute. The presence of noise suggests that is likely that the patient is not in cardiac arrest, although there may be some exceptions. As such, although an extended confirmation time is not considered an ideal treatment for a patient in VF, the odds are likely that it is a false detection so an extended confirmation time is reasonable. Since noise often self-terminates, but VF rarely does, extending the confirmation time when noise is suspected increases the discrimination between noise and VF.

As mentioned above, in some embodiments, high amplitude noise and high frequency noise may be treated differently for rhythm analysis and noise alerts. High amplitude noise tends to obliterate the ECG signal, making the other heart rate and other measurements meaningless, whereas high frequency noise may be rejected by other filters, so it may be better tolerated in the ECG analysis.

Figure 6:
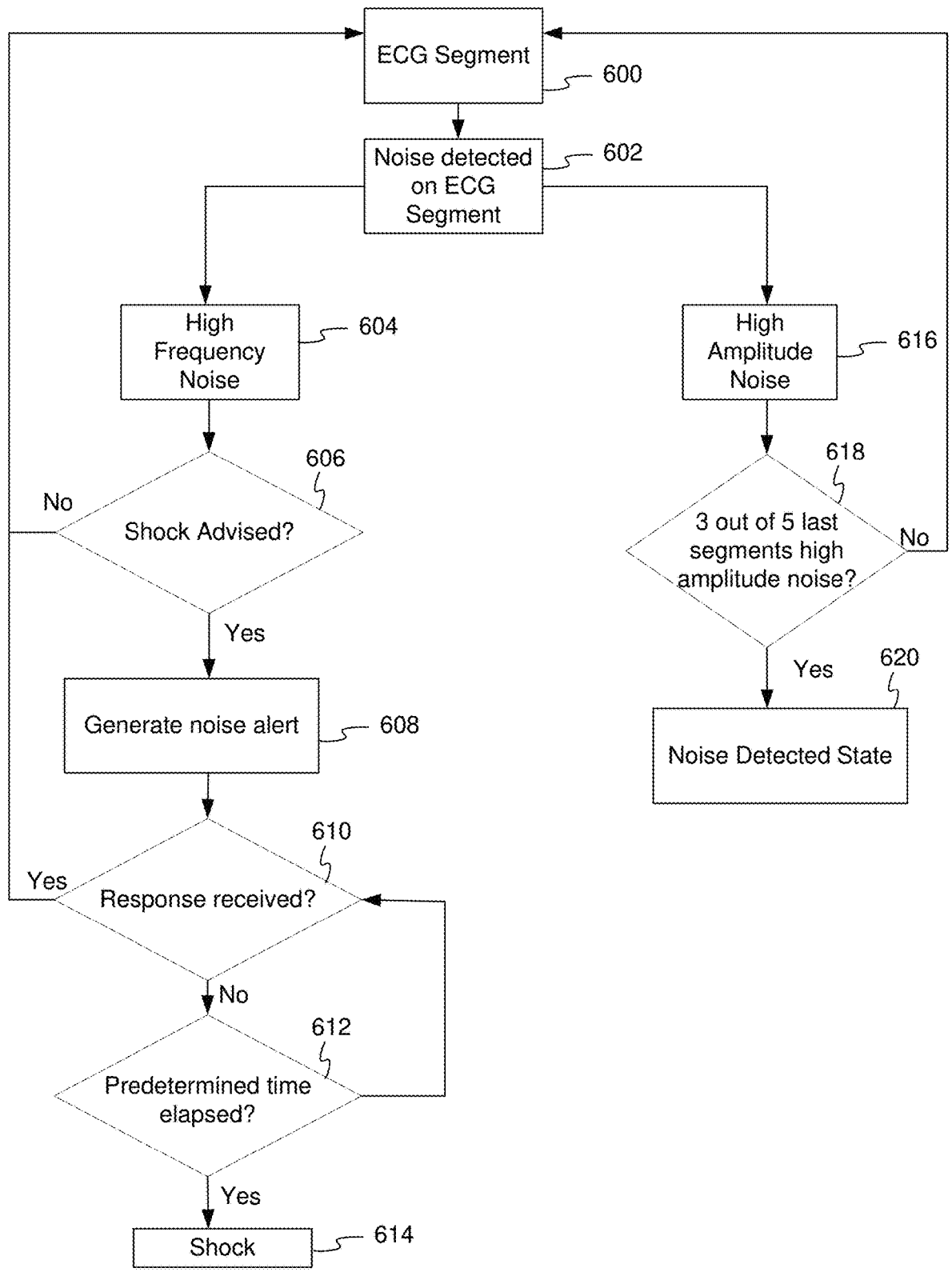
FIG. 6 is a flow chart illustrating another example process of alerting a patient when noise detected on an ECG signal based on the type of noise detected.

FIG. 6 illustrates an example process for generating noise and/or shock alerts based on high amplitude noise or high frequency noise. An ECG segment or signal is received at operation 600 and is determined if noise is detected in operation 602. If the noise is high frequency noise 604, then the processor 230 continues similar to that shown in FIG. 4. The processor 230 determines in operation 606 if a shock is advised. If not, the process returns to operation 600. If a shock is advised, a noise alert is generated at operation 608 and the processor 230 checks to see if a response has been received at the user interface 280 in operation 610. If a response has been received, then the shock is diverted. If a response has not been received, operation 612 determines if the predetermined time has elapsed. If so, then a shock is generated in operation 614. Otherwise, the process checks to see if a response has been received in operation 610.

If the noise is high amplitude noise 616, then the processor 230 determines if the last three out of five received ECG segments contained high amplitude noise at operation 618. If not, then additional ECG segments are received at operation 600. If yes, then the processor 230 may enter a noise detected state in operation 620, which is illustrated in further detail in FIG. 7. Alternatively, the noise state could be entered after a number of consecutive noisy detection (e.g. then), a fraction of noisy detections (e.g. four out of ten), when there is at least one noisy detection every second for a time period (e.g. 10 seconds), or other method of assessing a fraction of noisy detections over a period of time.

Figure 7:
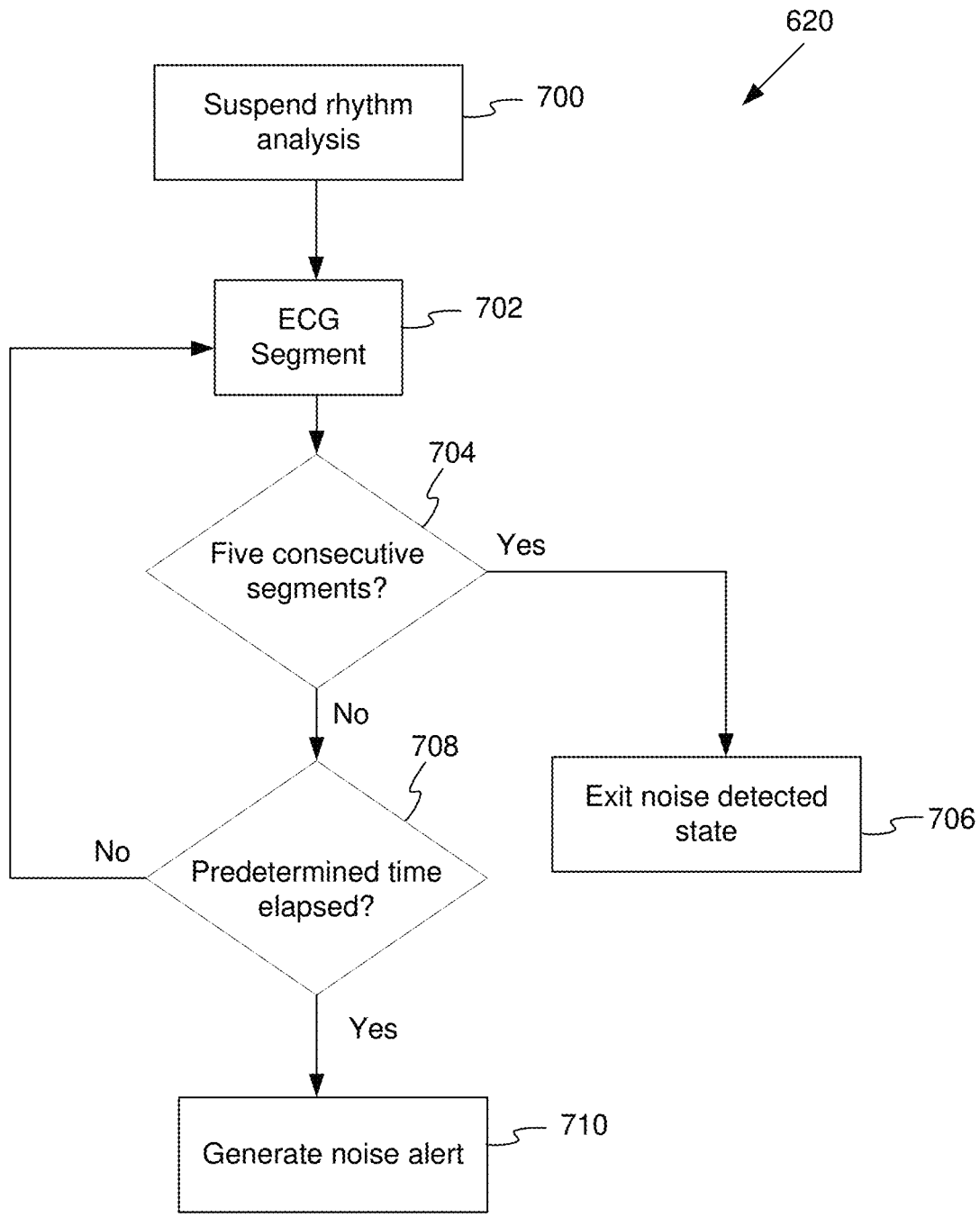
FIG. 7 is a flow chart illustrating the noise detected state of FIG. 6.

In FIG. 7, the high amplitude noise may be ignored for a predetermined amount of time since the noise may self-terminate. However, if the noise is present for an extended period of time, the patient should be alerted make adjustments to a garment or activity to clear up the noise. Sometimes the noise may be caused by activity on the part of the patient, a problem with a garment, a poor fit of the electrodes, or the electrodes are too dry. While it is desirable to alert the patient to noise, alerting the patient too quickly may bother the patient unnecessarily since the noise may go away if given enough time. During the delay, it is important not to give a false shock alert.

Accordingly, some embodiments of the disclosure suspend rhythm analysis for a period of time, and then alert the patient if the analysis is suspended for an extended period of time. For example, in FIG. 7, after entering the noise detected state of FIG. 6, rhythm analysis is suspended at operation 700 and additional ECG segments are received at operation 702. The process determines if five consecutive segments have been received without noise at operation 704. Although five consecutive segments are shown in FIG. 7, other numbers of segments may be used. The criteria for exiting the noise state could also be expressed in other terms. For example, if ten seconds elapses without any noise detection, then the noise detected state is exited. The purpose to confirm the ECG signal is clean prior to performing rhythm analysis again. Accordingly, in some embodiments, more or less segments may be used, as desired. If five consecutive segments have been received without noise, then the noise detected state is exited at operation 706, as it is assumed the noise has cleared up, and the process returns to operation 600 in FIG. 6.

If five consecutive segments without noise have not been received at operation 704, then the process check if a predetermined time as elapsed at operation 708. The predetermined time may be between one and fifteen minutes, for example, to allow for the noise to self-terminate. If the predetermined time has not elapsed, then additional ECG segments are received at operation 702 until either the predetermined time has elapsed or five consecutive segments are received without noise. If the predetermined time elapses, in operation 710 a noise alert is generated, and the process then waits for either a confirmation time to elapse or a user response to be received, as discussed in detail above with respect to FIGS. 4-6.

The noise alerts discussed above in any of the embodiments may be generated by the processor 230 or the processor 230 may cause the user interface 280 to generate the noise alert to the user. The noise alert may be an audible alarm or a visual alarm. In some embodiments, the noise alert is either visually and/or audibly differently, allowing a user to know that there is an issue with noise interruption in the ECG signal. In some embodiments, however, the noise alert and the shock alert may be the same visual and/or audible alert. Further, the noise alert may also be sent to a remote device, such as a cell phone, computer, tablet, etc., in addition to, or instead of on the user interface 280.

Aspects and examples of the disclosure may operate on particularly created hardware, firmware, digital signal processors, or on a specially programmed computer including a processor operating according to programmed instructions. The terms controller or processor as used herein are intended to include microprocessors, microcomputers, Application Specific Integrated Circuits (ASICs), and dedicated hardware controllers. One or more aspects of the disclosure may be embodied in computer-usable data and computer-executable instructions, such as in one or more program modules, executed by one or more computers (including monitoring modules), or other devices. Generally, program modules include routines, programs, objects, components, data structures, etc. that perform particular tasks or implement particular abstract data types when executed by a processor in a computer or other device. The computer executable instructions may be stored on a computer readable storage medium such as a hard disk, optical disk, removable storage media, solid state memory, Random Access Memory (RAM), etc. As will be appreciated by one of skill in the art, the functionality of the program modules may be combined or distributed as desired in various aspects. In addition, the functionality may be embodied in whole or in part in firmware or hardware equivalents such as integrated circuits, field programmable gate arrays (FPGA), and the like. Particular data structures may be used to more effectively implement one or more aspects of the disclosure, and such data structures are contemplated within the scope of computer executable instructions and computer-usable data described herein.

The disclosed aspects and examples may be implemented, in some cases, in hardware, firmware, software, or any combination thereof. The disclosed aspects may also be implemented as instructions carried by or stored on one or more or computer-readable storage media, which may be read and executed by one or more processors. Such instructions may be referred to as a computer program product. Computer-readable media, as discussed herein, means any media that can be accessed by a computing device. By way of example, and not limitation, computer-readable media may comprise computer storage media and communication media.

Computer storage media means any medium that can be used to store computer-readable information. By way of example, and not limitation, computer storage media may include RAM, ROM, Electrically Erasable Programmable Read-Only Memory (EEPROM), flash memory or other memory technology, Compact Disc Read Only Memory (CD-ROM), Digital Video Disc (DVD), or other optical disk storage, magnetic cassettes, magnetic tape, magnetic disk storage or other magnetic storage devices, and any other volatile or nonvolatile, removable or non-removable media implemented in any technology. Computer storage media excludes signals per se and transitory forms of signal transmission.

Communication media means any media that can be used for the communication of computer-readable information. By way of example, and not limitation, communication media may include coaxial cables, fiber-optic cables, air, or any other media suitable for the communication of electrical, optical, Radio Frequency (RF), infrared, acoustic or other types of signals.

Aspects and examples of the present disclosure operate with various modifications and in alternative forms. Specific aspects have been shown by way of example in the drawings and are described in detail herein below. However, it should be noted that the examples disclosed herein are presented for the purposes of clarity of discussion and are not intended to limit the scope of the general concepts disclosed to the specific examples described herein unless expressly limited. As such, the present disclosure is intended to cover all modifications, equivalents, and alternatives of the described aspects in light of the attached drawings and claims.

References in the specification to embodiment, aspect, example, etc., indicate that the described item may include a particular feature, structure, or characteristic. However, every disclosed aspect may or may not necessarily include that particular feature, structure, or characteristic. Moreover, such phrases are not necessarily referring to the same aspect unless specifically noted. Further, when a particular feature, structure, or characteristic is described regarding a particular aspect, such feature, structure, or characteristic can be employed in connection with another disclosed aspect whether or not such feature is explicitly described in conjunction with such other disclosed aspect.

EXAMPLES

Illustrative examples of the technologies disclosed herein are provided below. An embodiment of the technologies may include any one or more, and any combination of, the examples described below.

Example 1 is a wearable cardioverter defibrillator (WCD), comprising a support structure configured to be worn by an ambulatory patient; an energy storage module configured to store an electrical charge; a discharge circuit coupled to the energy storage module; electrodes configured to render an electrocardiogram (ECG) signal of the patient while the patient is wearing the support structure; a user interface configured to output an alarm in response to a noise alarm signal; and a processor. The processor is configured to receive the ECG signal, determine whether noise is present on the ECG signal, determine from the ECG signal whether a shock criterion is met, and cause the user interface to generate the noise alarm signal when the noise is present on the ECG signal and the shock criterion is met and not generate the noise alarm signal when noise is present on the ECG signal and the shock criterion is not met.

Example 2 is the WCD of example 1, wherein the processor is further configured to receive an additional ECG signal for a predetermined time after the shock criterion is met; determine whether noise is present on the additional ECG signal; and when the noise is determined to be present on the additional ECG signal, generate the noise alarm signal.

Example 3 is the WCD of example 2, wherein the predetermined amount of time is between five seconds and fifteen minutes.

Example 4 is the WCD of any one of examples 1-3, wherein the user interface is further configured to receive an input from a user, and wherein the processor is further configured to control the discharge circuit to discharge a stored charge if the input from the user input is not received within a predetermined amount of time after the noise alarm signal is generated.

Example 5 is the WCD of any one of examples 1-4, wherein the processor is further configured to detect QRS complexes in the ECG signal and determine noise is present on the ECG signal when a detected QRS complex is greater than a threshold.

Example 6 is the WCD of example 5, wherein the threshold is between 2-20 mV.

Example 7 is the WCD of any one of examples 1-6, wherein the processor is further configured to detect QRS complexes in the ECG signal and determine noise is present on the ECG signal when an amplitude of an unfiltered baseline shift in the vicinity of a detected QRS complex is larger than a threshold.

Example 8 is the WCD of example 7, wherein the threshold is between 2-20 mV.

Example 9 is the WCD of any one of examples 1-8, wherein the processor is further configured to detect QRS complexes in the ECG signal and determine noise is present on the ECG signal when a number of baseline crossings near a detected QRS complex is greater than a threshold.

Example 10 is the WCD of any one of examples 1-9, wherein the processor is further configured to detect QRS complexes in the ECG signal and determine noise is present on the ECG signal when a pulse width of a detected QRS complex is less than a threshold.

Example 11 is the WCD of any one of examples 1-10, further comprising a physical sensor configured to output a signal and wherein the processor is further configured to determine noise is present on the ECG signal when the signal from the physical sensor and the ECG signal are correlated.

Example 12 is the WCD of any one of examples 1-11, further comprising a physical sensor configured to output a signal and wherein the processor is further configured to detect a high rate of change on the signal; detect a QRS complex in the ECG signal; determine whether the high rate of change is coincident with the QRS complex; and determine noise is present on the ECG signal when the high rate of change is coincident with the QRS complex.

Example 13 is the WCD of any one of examples 1-12, wherein the alarm is an audible alarm.

Example 14 is a wearable cardioverter defibrillator (WCD), comprising a support structure configured to be worn by an ambulatory patient; an energy storage module configured to store an electrical charge; a discharge circuit coupled to the energy storage module; electrodes configured to render an electrocardiogram (ECG) signal of the patient while the patient is wearing the support structure; a user interface configured to output an alarm in response to a noise alarm signal; and a processor. The processor is configured to receive the ECG signal, determine whether high frequency noise or high amplitude noise is present on the ECG signal, determine from the ECG signal whether a shock criterion is met, cause the user interface to generate the noise alarm signal when the high frequency noise is present on the ECG signal and the shock criterion is met, and cause the user interface to not generate the noise alarm signal when the high frequency noise is present on the ECG signal and the shock criterion is not met, and when the noise is high amplitude noise, cause the user interface to generate the noise alarm signal when the high amplitude noise is present for a predetermined amount of time.

Example 15 is the WCD of example 14, wherein the processor is further configured to suspend analysis of the ECG signal to determine whether a shock criterion is met when the noise is high amplitude noise.

Example 16 is the WCD of example 15, wherein the processor is further configured to parse the ECG signal into a plurality of segments and suspend analysis of the ECG signal when at least at least a predetermined ratio of received segments of the ECG signal have high amplitude noise.

Example 17 is the WCD of example 16, wherein the processor is further configured to suspend analysis of the ECG signal until a predetermined ratio of ECG segments are determined to not have high amplitude noise or the predetermined time has elapsed and the noise alarm signal is generated.

Example 18 is the WCD of any one of examples 14-17, wherein the predetermined amount of time is between one and fifteen minutes.

Example 19 is the WCD of any one of examples 14-18, wherein the processor is further configured to receive an additional ECG signal for a predetermined time after the shock criterion is met; determine whether high frequency noise is present on the additional ECG signal; and when high frequency noise is determined to be present on the additional ECG signal, generate the noise alarm signal.

Example 20 is the WCD of example 19, wherein the predetermined amount of time is between five seconds and fifteen minutes.

Example 21 is the WCD of any one of examples 14-20, further comprising a user input configured to receive an input from a user, and wherein the processor is further configured to control the discharge circuit to discharge a stored electrical charge if the input from the user input is not received within a predetermined amount of time after the noise alarm signal is generated.

Example 22 is the WCD of any one of examples 14-21, wherein the processor is further configured to detect QRS complexes in the ECG signal and determine high amplitude noise is present on the ECG signal when a detected QRS complex is greater than a threshold.

Example 23 is the WCD of example 22, wherein the threshold is between 2-20 mV.

Example 24 is the WCD of any one of examples 14-23, wherein the processor is further configured to detect QRS complexes in the ECG signal and determine high amplitude noise is present on the ECG signal when an amplitude of an unfiltered baseline shift in the vicinity of a detected QRS complex is larger than a threshold.

Example 25 is the WCD of example 24, wherein the threshold is between 2-20 mV.

Example 26 is the WCD of any one of examples 14-25, wherein the processor is further configured to detect QRS complexes in the ECG signal and determine high frequency noise is present on the ECG signal when a number of baseline crossings near a detected QRS complex is greater than a threshold.

Example 27 is the WCD of any one of examples 14-26, wherein the processor is further configured to detect QRS complexes in the ECG signal and determine noise is present on the ECG signal when a pulse width of a detected QRS complex is less than a threshold.

Example 28 is the WCD of any one of examples 14-27, further comprising a physical sensor configured to output a signal and wherein the processor is further configured to determine noise is present on the ECG signal when the signal from the physical sensor and the ECG signal are correlated.

Example 29 is the WCD of any one of examples 14-28, further comprising a physical sensor configured to output a signal and wherein the processor is further configured to detect a high rate of change on the signal; detect a QRS complex in the ECG signal; and determine whether the high rate of change is coincident with the QRS complex; and determine noise is present on the ECG when the high rate of change is coincident with the QRS complex.

Example 30 is a method for alerting an ambulatory patient of noise on a wearable cardioverter defibrillator (WCD), comprising storing an electrical charge in an energy storage module; rendering an electrocardiogram (ECG) signal of the patient while the patient is wearing the support structure; determining whether noise is present on the ECG signal; determining from the ECG signal whether a shock criterion is met; and outputting an alarm at a user interface when the noise is present on the ECG signal and the shock criterion is met and not output the noise alarm signal when noise is present on the ECG signal and the shock criterion is not met.

Example 31 is the method of claim 30, further comprising receiving an additional ECG signal for a predetermined time after the shock criterion is met; determining whether noise is present on the additional ECG signal; and when the noise is determined to be present on the additional ECG signal, outputting the noise alarm signal.

Example 32 is the method of claim 31, wherein the predetermined amount of time is between five seconds and fifteen minutes.

Example 33 is the method of any one of examples 30-32, wherein the user interface is further configured to receive an input from a user, and wherein the processor is further configured to control the discharge circuit to discharge a stored charge if the input from the user input is not received within a predetermined amount of time after the noise alarm signal is generated.

Example 34 is the method of any one of examples 30-33, further comprising detecting QRS complexes in the ECG signal and determining noise is present on the ECG signal when a detected QRS complex is greater than a threshold.

Example 35 is the method of example 34, wherein the threshold is between 2-20 mV.

Example 36 it the method of any one of examples 30-35, further comprising detecting QRS complexes in the ECG signal and determining noise is present on the ECG signal when an amplitude of an unfiltered baseline shift in the vicinity of a detected QRS complex is larger than a threshold.

Example 37 is the method of example 36, wherein the threshold is between 2-20 mV.

Example 38 is the method of any one of examples 30-37, further comprising detecting QRS complexes in the ECG signal and determining noise is present on the ECG signal when a number of baseline crossings near a detected QRS complex is greater than a threshold.

Example 39 is the method of any one of examples 30-38, further comprising detecting QRS complexes in the ECG signal and determining noise is present on the ECG signal when a pulse width of a detected QRS complex is less than a threshold.

Example 40 is the method of any one of examples 30-39, determining noise is present on the ECG signal when a signal from a physical sensor and the ECG signal are correlated.

Example 41 it the method of any one of examples 30-40, further comprising detecting a high rate of change on a signal from a physical sensor; detecting a QRS complex in the ECG signal; determining whether the high rate of change is coincident with the QRS complex; and determining noise is present on the ECG signal when the high rate of change is coincident with the QRS complex.

Example 42 is the method of any one of examples 30-41, wherein the alarm is an audible alarm.

Example 43 is a method for alerting an ambulatory patient of noise on a wearable cardioverter defibrillator (WCD), comprising storing an electrical charge in an energy storage module; rendering an electrocardiogram (ECG) signal of the patient while the patient is wearing the support structure; determining whether high frequency noise or high amplitude noise is present on the ECG signal; when the noise is high frequency noise, determining from the ECG signal whether a shock criterion is met, outputting a noise alarm signal when the high frequency noise is present on the ECG signal and the shock criterion is met, and not outputting the noise alarm signal when the high frequency noise is present on the ECG signal and the shock criterion is not met, and when the noise is high amplitude noise, outputting the noise alarm signal when the high amplitude noise is present for a predetermined amount of time.

Example 44 is the method of example 43, further comprising suspending analysis of the ECG signal to determine whether a shock criterion is met when the noise is high amplitude noise.

Example 45 is the method of example 44, further comprising parsing the ECG signal into a plurality of segments and suspending analysis of the ECG signal when at least at least a predetermined ratio of received segments of the ECG signal have high amplitude noise.

Example 46 is the method of either example 44 or 45, further comprising suspending analysis of the ECG signal until a predetermined ratio of ECG segments are determined to not have high amplitude noise or the predetermined time has elapsed and the noise alarm signal is generated.

Example 47 is the method of any one of examples 43-46, wherein the predetermined amount of time is between one and fifteen minutes.

Example 48 is the method of any one of examples 43-47, further comprising receiving an additional ECG signal for a predetermined time after the shock criterion is met; determining whether high frequency noise is present on the additional ECG signal; and when high frequency noise is determined to be present on the additional ECG signal, outputting the noise alarm signal.

Example 49 is the method of example 48, wherein the predetermined amount of time is between five seconds and fifteen minutes.

Example 50 is the method of any one of examples 43-49, further comprising receiving an input from a user, and discharging the stored electrical charge if the input from the user input is not received within a predetermined amount of time after the noise alarm signal is output.

Example 51 is the method of any one of examples 43-50, further comprising detecting QRS complexes in the ECG signal and determining high amplitude noise is present on the ECG signal when a detected QRS complex is greater than a threshold.

Example 52 is the method of example 51, wherein the threshold is between 2-20 mV.

Example 53 is the method of any one of examples 43-52, further comprising detecting QRS complexes in the ECG signal and determining high amplitude noise is present on the ECG signal when an amplitude of an unfiltered baseline shift in the vicinity of a detected QRS complex is larger than a threshold.

Example 54 is the method of example 53, wherein the threshold is between 2-20 mV.

Example 55 is the method of any one of examples 43-54, further comprising detecting QRS complexes in the ECG signal and determining high frequency noise is present on the ECG signal when a number of baseline crossings near a detected QRS complex is greater than a threshold.

Example 56 is the method of any one of examples 43-55, further comprising detecting QRS complexes in the ECG signal and determining noise is present on the ECG signal when a pulse width of a detected QRS complex is less than a threshold.

Example 57 is the method of any one of examples 43-56, further comprising determining noise is present on the ECG signal when a signal from a physical sensor and the ECG signal are correlated.

Example 58 is the method of any one of examples 43-46, further comprising detecting a high rate of change on a signal from a physical sensor; detecting a QRS complex in the ECG signal; determining whether the high rate of change is coincident with the QRS complex; and determining noise is present on the ECG when the high rate of change is coincident with the QRS complex.

Example 59 is a wearable cardioverter defibrillator (WCD), comprising a support structure configured to be worn by an ambulatory patient; an energy storage module configured to store an electrical charge; a discharge circuit coupled to the energy storage module; electrodes configured to render an electrocardiogram (ECG) signal of the patient while the patient is wearing the support structure; a user interface configured to output an alarm in response to a noise alarm signal; and a processor. The processor is configured to receive an ECG signal, determine when high amplitude noise is present on the ECG signal, and suspend ECG analysis when high amplitude noise persists for more than a predetermined amount of time.

Example 60 is the WCD of example 59, wherein the processor is further configured to cause the user interface to provide a patient alert if the ECG analysis is suspended for more than a predetermined amount of time.

Example 61 is the WCD of example 60, wherein the predetermined amount of time is between one and fifteen minutes.

Example 62 is the WCD of example 60, wherein the processor is further configured to parse the ECG signal into a plurality of segments and suspend analysis of the ECG signal when at least a predetermined ratio of received segments of the ECG signal have high amplitude noise.

Example 63 is the WCD of example 62, wherein the processor is further configured to suspend analysis of the ECG signal until a predetermined ratio of ECG segments are determined to not have high amplitude noise or the predetermined time has elapsed and the noise alarm signal is generated.

Example 64 is the WCD of any one of examples 59-63, wherein the processor is further configured to detect QRS complexes in the ECG signal and determine high amplitude noise is present on the ECG signal when an unfiltered baseline shift in the vicinity of a detected QRS complex is larger than a pre-determined threshold.

Example 66 is the WCD of example 65, wherein the pre-determined threshold is between 2-20 mV.

Example 67 is the WCD of any one of examples 59-66, wherein the processor is further configured to detect QRS complexes in the ECG signal and determine high amplitude noise is present on the ECG signal when a detected QRS complex is greater than a threshold.

Example 68 is the WCD of claim 67, wherein the threshold is between 2-20 mV.

Example 69 is the wearable cardioverter defibrillator (WCD), comprising a support structure configured to be worn by an ambulatory patient; an energy storage module configured to store an electrical charge; a discharge circuit coupled to the energy storage module; electrodes configured to render an electrocardiogram (ECG) signal of the patient while the patient is wearing the support structure; a user interface configured to output an alarm in response to a noise alarm signal; and a processor. The processor is configured to receive an ECG signal, determine when high frequency noise is present on the ECG signal, determine when shock criteria are met, provide a confirmation time when shock criteria are met, and provide an extended confirmation time when high frequency noise is present.

Example 70 is the WCD of example 69, wherein the processor is further configured to detect QRS complexes in the ECG signal and determine high frequency noise is present on the ECG signal when a number of baseline crossings near a detected QRS complex is greater than a pre-determined threshold.

Example 71 is the WCD of either example 69 or 70, wherein the processor is further configured to detect QRS complexes in the ECG signal and determine noise is present on the ECG signal when a pulse width of a detected QRS complex is less than a threshold.

The previously described versions of the disclosed subject matter have many advantages that were either described or would be apparent to a person of ordinary skill. Even so, these advantages or features are not required in all versions of the disclosed apparatus, systems, or methods.

Additionally, this written description makes reference to particular features. It is to be understood that the disclosure in this specification includes all possible combinations of those particular features. Where a particular feature is disclosed in the context of a particular aspect or example, that feature can also be used, to the extent possible, in the context of other aspects and examples.

Also, when reference is made in this application to a method having two or more defined steps or operations, the defined steps or operations can be carried out in any order or simultaneously, unless the context excludes those possibilities.

Although specific examples of the disclosure have been illustrated and described for purposes of illustration, it will be understood that various modifications may be made without departing from the spirit and scope of the disclosure. Accordingly, the disclosure should not be limited except as by the appended claims.

We claim:

1. A wearable cardioverter defibrillator (WCD), comprising:
    a support structure configured to be worn by an ambulatory patient;
    an energy storage module configured to store an electrical charge;
    a discharge circuit coupled to the energy storage module;
    electrodes configured to render an electrocardiogram (ECG) signal of the patient while the patient is wearing the support structure;
    a user interface configured to output an alarm in response to a noise alarm signal; and
    a processor configured to:
        receive the ECG signal,
        determine whether noise is present on the ECG signal,
        determine from the ECG signal whether a shock criterion is met,
        cause the user interface to generate the noise alarm signal when the noise is present on the ECG signal and the shock criterion is met and not generate the noise alarm signal when noise is present on the ECG signal and the shock criterion is not met,
        receive an additional ECG signal for a predetermined time after the shock criterion is met,
        determine whether noise is present on the additional ECG signal, and
        when the noise is determined to be present on the additional ECG signal, generate the noise alarm signal.

2. The WCD of claim 1, wherein the predetermined amount of time is between five seconds and fifteen minutes.

3. The WCD of claim 1, wherein the user interface is further configured to receive an input from a user, and wherein the processor is further configured to control the discharge circuit to discharge a stored charge if the input from the user input is not received within a predetermined amount of time after the noise alarm signal is generated.

4. The WCD of claim 1, wherein the processor is further configured to detect QRS complexes in the ECG signal and determine noise is present on the ECG signal when an amplitude of an unfiltered baseline shift in the vicinity of a detected QRS complex is larger than a threshold.

5. The WCD of claim 4, wherein the threshold is between 2-20 mV.

6. The WCD of claim 1, wherein the processor is further configured to detect QRS complexes in the ECG signal and determine noise is present on the ECG signal when a number of baseline crossings near a detected QRS complex is greater than a threshold.

7. The WCD of claim 1, wherein the processor is further configured to detect QRS complexes in the ECG signal and determine noise is present on the ECG signal when a pulse width of a detected QRS complex is less than a threshold.

8. The WCD of claim 1, further comprising a physical sensor configured to output a signal and wherein the processor is further configured to determine noise is present on the ECG signal when the signal from the physical sensor and the ECG signal are correlated.

9. The WCD of claim 1, further comprising a physical sensor configured to output a signal and wherein the processor is further configured to:
    detect a high rate of change on the signal;
    detect a QRS complex in the ECG signal;
    determine whether the high rate of change is coincident with the QRS complex; and
    determine noise is present on the ECG signal when the high rate of change is coincident with the QRS complex.

10. The WCD of claim 1, wherein the alarm is an audible alarm.

11. The WCD of claim 1, wherein the processor is further configured to detect QRS complexes in the ECG signal and determine noise is present on the ECG signal when an amplitude of the detected QRS complex is greater than a threshold.

12. The WCD of claim 11, wherein the threshold is between 2-20 mV.

* * * * *